United States Patent
Alimonti et al.

(10) Patent No.: US 9,668,961 B2
(45) Date of Patent: Jun. 6, 2017

(54) SCREENING METHOD AND SUBSTANCES FOR CONTRASTING AGING

(71) Applicant: Andrea Alimonti, Milan (IT)

(72) Inventors: Andrea Alimonti, Milan (IT); Ivana Matic, Rome (IT)

(73) Assignee: Andrea Alimonti, Milan (IT)

( * ) Notice: Subject to any disclaimer, the term of this patent is extended or adjusted under 35 U.S.C. 154(b) by 0 days.

(21) Appl. No.: 14/515,839

(22) Filed: Oct. 16, 2014

(65) Prior Publication Data

US 2016/0106661 A1    Apr. 21, 2016

(51) Int. Cl.
| | |
|---|---|
| *A61K 36/537* | (2006.01) |
| *A61K 8/97* | (2017.01) |
| *A61Q 19/08* | (2006.01) |
| *A61Q 19/00* | (2006.01) |
| *A61K 36/232* | (2006.01) |
| *A61K 36/48* | (2006.01) |
| *A61K 36/53* | (2006.01) |
| *A61K 36/63* | (2006.01) |

(52) U.S. Cl.
CPC .............. *A61K 8/97* (2013.01); *A61K 36/232* (2013.01); *A61K 36/48* (2013.01); *A61K 36/53* (2013.01); *A61K 36/537* (2013.01); *A61K 36/63* (2013.01); *A61Q 19/00* (2013.01); *A61Q 19/08* (2013.01); *A61K 2236/30* (2013.01); *A61K 2236/33* (2013.01)

(58) Field of Classification Search
None
See application file for complete search history.

(56) References Cited

FOREIGN PATENT DOCUMENTS

EP    2762131    8/2014

OTHER PUBLICATIONS

Almanza et al. (1997) Tetrahedron, vol. 53, No. 43, pp. 14719-14728.*
Blaney et al. (1988) Entomol. exp. appl. 46: 267-274.*
Sosa et al. (1994) Journal of Natural Products, vol. 57, No. 9, pp. 1262-1265.*
Website document entitled: "Salvia haenkei—Prawn Sage" (available at http://www.fbts.com/salvia-haenkei.html?printable=Y). Downloaded from website May 20, 2016.*
EPO search report and opinion for related EP 14153316.6, five pages (Apr. 2014).
Almanza et al. "Clerodane diterpenoids and an ursane triterpenoid from Salvia haenki. Computer-assisted structural elucidation" *Tetrahedron*, vol. 53, No. 43, pp. 14719-14728 (Oct. 1997).
Fengmei et al. "A study of scavenging effects of Chinese medicine on superoxide anion radicals by pule radiolysis" *Radiation Physics and Chemistry*, vol. 42, No. 4-6, pp. 1031-1034 (Oct.-Dec. 1993).
Fournet et al. "Leishmanicidal and trypanocidal activities of Bolivian medicinal plants" *Journal of Ethnopharmacology*, vol. 41, No. 1-2, pp. 19-37 (Jan. 1994).
Topcu "Bioactive triterpenoids from *Salvia* species" *Journal of Natural Products*, vol. 69, No. 3, pp. 482-487 (Mar. 2006).

* cited by examiner

*Primary Examiner* — Chris R Tate
*Assistant Examiner* — Russell Fiebig
(74) *Attorney, Agent, or Firm* — Nixon & Vanderhye PC (57) ABSTRACT

The present invention refers to a novel in vitro method for detecting anti-senescence or pro-senescence activity of a compound, and to compounds with anti-senescence activity detected by said method, in particular to *Salvia Haenkei* extracts, and to compositions comprising said extracts.

6 Claims, 9 Drawing Sheets

SCREENING METHOD AND SUBSTANCES FOR CONTRASTING AGING

This application is related to IT Application No. RM2013A000063, filed 31 Jan. 2013, and EP Application No. 14153316.6, filed 30 Jan. 2014.

The present invention refers to a novel in vitro method for detecting anti-senescence or pro-senescence activity of a compound, and to compounds with anti-senescence activity detected by said method, in particular to *Salvia Haenkei* extracts, and to compositions comprising said extracts.

STATE OF THE PRIOR ART

Cellular senescence is an irreversible cell growth arrest that happens in all cells of the human organism during aging. Most cells cannot divide indefinitely due to the progressive shortness of their telomeres. Indeed, after only 50-60 population doublings (Haflick limit) cells stop their growth, even though they continue to metabolize and produce ATP.

Cells can become senescent prematurely as a result of stressful insults such as oncogenes, tumour suppressor genes loss and DNA damage (induced by UV radiation or by oxidative stress such as after ROS accumulation). This phenomenon is referred to as premature senescence since it occurs rapidly after the driving event occurs.

Recent studies identified a novel type of cellular senescence response, which occurs acutely after inactivation of the tumour suppressor PTEN, an essential regulator of the PI3K pathway in mouse and human primary cells. Importantly, senescence can also occur in cancer cells which have completely lost PTEN, or can be induced in human cancer cells after pharmacological inhibition of PTEN (Alimonti et al. J Clin Invest. 2010, 681-93 and Lin H K et al. Nature 2010, 464(7287):374-9).

Therefore, PTEN and additional senescence relevant genes can be targeted for pro-senescence therapy for cancer.

The PI3K/AKT pathway is also implicated in replicative senescence and aging. Indeed, inhibition of mTOR, a fundamental component of this pathway, can prevent senescence by blocking p53 and decrease aging in a mouse model (Alimonti et al. J Clin Invest. 2010). This is confirmed in a recent study, where rapamycin—an inhibitor of mTOR, when administered late in life, extend the lifespan of treated mice. The PI3K/AKT pathway is also implicated in UV induced cellular senescence (photoaging). Indeed, recent findings show that UV irradiation can activate AKT and mTOR, thus boosting senescence.

Photoaging in skin is mostly a consequence of exposure to UV irradiation during lifetime, and is characterized by wrinkling, pigment changes, cracking and loss of elasticity of the skin.

Similarly, exposure of skin to radiation other than UV, such as during X-radiation (e.g., during radiotherapy treatments for cancer), can result in acute side effects that might entail limiting the treatment. Typically, the skin starts to become pink and sore into radiation treatment. The reaction may become more severe during the treatment and for up to about one week following the end of radiotherapy.

Since it is believed that cellular senescence is an essential (causative) element of aging, scientific research is focusing on the development of effective therapies for preventing and delaying cellular senescence. However, only few compounds have shown potent anti-senescent effects in vivo, and several efforts have been made to develop assays for the identification of novel anti-senescence compounds.

Given the relevance of cellular senescence for pathologies such as cancer and aging, the need for a method that allows for a rapid and effective identification of novel pro- and anti-senescence compounds is greatly felt.

In PCT Patent Application WO2009046436 (Alimonti et al.), Oct. 6, 2008, it is described a Pten null (Pten$^{-/-}$) MEF cells-based screening method for assessing the ability of a compound to alter the senescence state of a cell. Indeed, to assess candidate compounds, Pten$^{Lx/Lx}$ MEF cells must be infected with retro-viral Cre vectors, then selected for 2 days and finally plated for the experiment. The possibility that the infection be optimal is generally of 50% of the cases, and quite often the percent of infected cells is very low. This markedly reduces the number of candidate compounds that can be tested in the assay. Moreover, Pten$^{Lx/Lx}$ MEF cells must be continuously regenerated by crossbreeding Pten$^{Lx/Lx}$ mice. These mice are subsequently sacrificed to obtain the MEF cells (or "MEFs") needed for the assay.

It is an object of the present invention to provide a method for detecting the anti-senescence or pro-senescence activity of a compound solving the above-mentioned advantages.

SUMMARY OF THE INVENTION

The present invention refers to a novel in vitro method for detecting the anti-senescence or pro-senescence activity of a compound, and to the compounds with anti-senescence activity detected by such method. The method of the invention affords the advantage of a quick, inexpensive in vitro screening method that can easily be automated, since engineered cell lines are utilized which, besides lacking a Pten functional gene, are reversibly immortalized.

Therefore, a first object of the present invention is a method for detecting the anti-senescence or pro-senescence activity of a candidate compound, comprising the following steps:
a) providing an engineered cell line, reversibly immortalized and lacking a functional Pten gene;
b) bringing said cell line back to a non-immortalized state;
c) contacting said cells, not immortalized anymore, with said candidate compound;
d) assessing the cellular proliferation of said cells following contact with said compound, so that an increase in cellular proliferation denotes an anti-senescence activity and a reduction in cellular proliferation denotes a pro-senescence activity.

A second object of the invention is a cosmetic use of a *Salvia Haenkei* extract as anti-aging substance.

A third object of the invention is a cosmetic composition comprising a *Salvia Haenkei* extract and one or more cosmetically acceptable carriers.

A fourth object of the invention is a *Salvia Haenkei* extract for use in the treatment of diseases associated with cellular aging.

Further advantages, as well as the features and the operation steps of the present invention will be made apparent in the following detailed description of some preferred embodiments thereof.

DETAILED DESCRIPTION OF THE FIGURES

FIG. 2 is a diagram showing the compounds found positive. In total, 1465 compounds were tested, of which: 1000 chemicals, 313 plant extracts and 152 marine extracts. In contrast with the chemicals, that showed a very low percentage of anti-senescence active principles (8 to 1000), the natural compounds demonstrated to be a precious source of anti-senescence active principles (18 active extracts have a statistically significant effect on one or more of the parameters utilized in the screening assay, as represented in FIG. 2). The criterion for singling out the anti-senescence compounds is based on the assessment of the growth of cells in contact with that given compound and on the percentage of cells positive to β-gal. Cells not subjected to senescence induction due to Pten gene nullification continue proliferating in the culture and their number is higher than that of cells that enter senescence and arrest proliferation (control). An increase of ≥40% in the growth in treated cells with respect to untreated control is considered a significant indicator of a potential anti-senescence effect of the compounds. In FIG. 2, 18 compounds able to increase Pten$^{-/-}$ cells growth in a statistically significant way (a growth increase of 40% or more) are represented. These compounds have then been tested for the expression of β-Galactosidase, a marker of senescence induction; *Salvia Haenkei* extract confirmed its anti-senescence activity, therefore it was tested in further photoaging tests and in replicative senescence models.

DETAILED DESCRIPTION OF THE INVENTION

The present invention is comprised of the following aspects, described in detail below.

The in vitro method enables to detect the anti-senescence or pro-senescence activity of a candidate compound such as a natural extract or a synthetic compound.

The method comprises a first step a), in which it is provided a cell line engineered so to be able to be reversibly immortalized, lacking a functional Pten gene (pten null $^{(-/-)}$). In a preferred embodiment said cells are obtained from MEF (Mouse Embryonic Fibroblast) cells isolated and cultivated from fetuses of homozygous PTEN IxP/IxP mice harvested from 13-day pregnant mice (mice of this type are identified, e.g. by reference code Jax Lab B6.129S4-Pten tm1Hwu/J-Homozygous for Ptentm1Hwu) Isolated cells can be made Pten null with a retro-viral Cre vector; examples of suitable vectors are the Cre-recombinase vectors. Cells can be reversibly immortalized by transfection with suitable vectors, preferably a doxocycline-inducible retro-viral vector could be used, such as, e.g., a TRIPZI-shp53 lentiviral vector (doxocycline (DOXO) inducible). The same result can be obtained if PTEN IxP/IxP MEFs are first infected with TRIPZI-shp53 and subsequently with Cre-recombinase vectors.

In the second step b), the cell line provided at step a) is brought back to a non-immortalized state. In an embodiment the cells will be made non-immortalized by p53 gene reactivation following removal of doxocycline from the culture medium. Therefore, there is no need to continuously infect primary Pten Lx/Lx MEFs and unnecessarily sacrifice animals. Moreover, since MEFs in the presence of doxocycline are immortalized, millions of cells can easily be plated on which to test thousands of compounds and extracts, plating as many cells as necessary for the screening. p53 reactivation cause cells to re-enter senescence from day 2. The peak of β-galactosidase positive and arrested cells is had at day 9 after doxocycline removal.

In the third step c) of the method, the candidate compound, of which any anti- or pro-senescence activity is to be detected, is contacted with the cells prepared at b). Compounds and extracts can e.g. be administered to cells from 1-3 days after DOXO removal.

In the fourth step d) of the method, cellular proliferation of cells following contact with the candidate compound to be analyzed is assessed. Assessment of the pro- or anti-senescence effect of the candidate compound could be carried out on the basis of the cellular proliferation assessed, e.g., with a cytological staining assay, utilizing the Crystal violet dye and/or determining at the same time β-galactosidase expression of the cells following contact with the candidate compound. Compounds that increase the proliferation of the PTEN$^{-/-}$ cells (assessed, e.g. by using the standard Crystal violet staining assay) and/or decrease their β-galactosidase activity are considered anti-senescence, whereas compounds that decrease the proliferation of the PTEN$^{-/-}$ cells and/or increase their β-galactosidase activity, are considered pro-senescence.

In an embodiment the method comprises a further step e) in which the candidate compound is contacted with engineered Pten$^{-/-}$ cells and engineered Pten$^{+/+}$ (wild type) cells, obtained as previously described, and a step f) in which the cellular proliferation of said cells following contact with said compound is assessed. These further steps enable to assess the specificity of the selected compounds/extracts. In an embodiment the candidate compounds are subsequently tested for their efficacy at different dosages (e.g., five different increasing concentrations).

In an embodiment the anti-senescence compounds are then tested for their efficacy to prevent additional types of senescence, in 3 known in vitro models: 1) replicative senescence in primary human fibroblast cells; 2) UV-induced senescence in human primary cells; 3) Episkin model.

In an embodiment the compounds selected as pro-senescence are also tested for their efficacy to induce senescence in: 1) human cancer cell lines; 2) cancer stem cells from murine and human cancers; 3) in vivo validation in pre-clinical murine models.

The inventors, by utilizing the method of the present description, have surprisingly discovered that the extract from the plant *Salvia Haenkei* (also known as Prawn Sage or Prawn Chorus and denoted in the present description also by the abbreviation HAEN) is particularly effective as anti-aging compound. The anti-aging properties of *Salvia Haenkei* extract have been further confirmed also in other in vitro assays, as described in detail in the experimental section of the present description.

Therefore, it is an object of the present invention the cosmetic use of an extract from *Salvia Haenkei* as anti-aging substance and cosmetic compositions comprising an extract from *Salvia Haenkei* and one or more cosmetically acceptable carriers. The extract could be prepared according to the methods known to a technician in the field, e.g. by plant material pre-extraction with hexane followed by extraction with methanol, or by ethanolic extraction with mechanical pre-extraction. For extraction, generally the following parts of the plant are used: stalk, leaves, flowers or mixtures thereof.

Cosmetically acceptable carriers are well-known in the art and could be selected on the basis of the final use of the application. For instance, the carriers of the present invention comprise, but are not limited to those suitable for application on skin. Such carriers are well-known to those skilled in the art and can include one or more diluents suitable for application on skin. The exact amount of carrier could depend on the amount of other optional ingredients included in the composition. E.g., in the compositions of the present invention the carrier may be from about 75 to about 99.99% by weight of the composition.

The compositions could be formulated in a number of ways, including but not limited to emulsions. For instance, suitable emulsions include oil-in-water emulsions, water-in-oil, water-in-oil-in-water, oil-in-water-in-oil and oil-in-water-in-silicone emulsions. Preferred compositions comprise oil-in-water emulsions.

The compositions of the present invention can be formulated in a variety of product types, including shampoos, creams, waxes, pastes, lotions, milks, mousses, gels, oils, emulsions and sprays. Preferred compositions are formulated in oil, suspension, emulsion, cream, spray, ointment, powder, gel, serum or liquid. These forms of product can be used for a number of applications, including but not limited to hand and body lotions, face moisturizing creams, anti acne creams, eye-shadows, lipsticks, sun creams and the like. Possible additional components needed to formulate such products vary with the product type and can be selected by the technician in the field on the basis of the known art. The compositions could comprise moisturizing, emollient and humectant agents, e.g. oils, fats, waxes, esters, alcohols, fatty acids, fatty acid ethoxylates, glycols, sugars, hyaluronic acid, cyclomethicone, and the like. Further examples can be found in the International Cosmetic Ingredient Dictionary, CTFA. The compositions of the present invention could be formulated both for topical and systemic administration (e.g. oral, intravenous, transmucosal or intramuscular) depending on the final application. Compositions in oral form are, e.g., capsules, tablets, lozenges, powders, granules.

The compositions according to the present invention will comprise, e.g., between 0.001 and 45%, preferably between 0.01 and 4% of extract.

The formulation can also comprise components that are selected depending on the carrier and/or the utilization provided for by the formulation. Further components include, but are not limited to antioxidants, chelating agents, emulsion stabilizers, preservatives, perfumes, aromatizing agents, humectants, waterproofing agents, cationic polymers, anionic polymers, vitamins, and the like. The compositions can comprise one or more additional active components, to make a composition both cosmetic or pharmaceutical.

According to a preferred embodiment, the compositions of the invention could further comprise extracts of Sage, Rosemary, *Galega officinalis*, Lavender, *Angelica archangelica*, *Olea europaea* and/or Imperatonin.

The *Salvia Haenkei* extract and the compositions of the present invention could be used as cosmetics for preventing and/or slowing down cellular aging not linked to pathological conditions, or for use in the treatment (meant also as prevention) of diseases associated with cellular aging.

The cosmetic use comprises, e.g., the improvement and/or the prevention of (skin) cutaneous aging signs such as wrinkling, decrease of skin softness and/or luminosity and the like, the improvement and/or the prevention of signs of aging of hair, nails, oral mucosae (gingival tissues included) and of the vaginal mucosa.

Examples of diseases associated with cellular aging which can be treated with the extract and the compositions of the present invention are, e.g., progeria, osteoarthritis, atherosclerosis, senile dementia and tumours, like e.g. gastrointestinal and prostate tumours.

In the present description, by the wording "diseases associated with cellular aging" there are meant also diseases whose treatment involves a cellular aging as a side effect, such as, e.g., the treatment of tumour disease with X-radiation, which causes photoaging, and/or chemiotherapics.

It is an object of the present invention also a method for the preparation of an extract from *Salvia Haenkei* comprising the following steps:

a) preparing a dry extract from *Salvia Haenkei* leaves, stalk and/or flowers;

b) subjecting the dry extract of step a) to one or more steps of extraction by organic solvent, like, e.g., ethanol and/or methanol;

c) totally or partially eliminating the organic solvent from the extract obtained at point b), and optionally performing one or more filtering and/or concentrating steps.

According to an embodiment, the method for the preparation of a natural extract from *Salvia Haenkei*, e.g. for cosmetic use, comprises the following steps: preparing *Salvia Haenkei* fresh or dried leaves, flowers and/or stalk, macerating the *Salvia Haenkei* preparation in vegetable oil or glycerine, or extracting the *Salvia Haenkei* preparation by steam distillation. According to a preferred embodiment, the vegetable oil and the vegetable glycerine for maceration are organic and the water for extraction by steam distillation is mineral or thermal.

Examples aimed at better illustrating the methods disclosed in the present description are reported below; such examples are in no way to be considered as a limitation of the preceding description and of the subsequent claims.

EXAMPLES

Example 1 Screening Method for Identifying Compounds with Pro- or Anti-Senescence Activity Step 1

In the first step, the compounds of which the pro- or anti-senescence activity is to be determined are added in single concentration (0.01 mg/ml) to immortalized Pten null (Pten$^{-/-}$) MEF cells (or "MEFs"). These cells are obtained from homozygous PTEN IxP/IxP mice. PTEN LxP/LxP mice are crossbred and fetuses harvested at 13.5 dpc. Individual MEFs are produced and cultivated following the standard protocols described, e.g., in Alimonti et al. J Clin Invest. 2010.

PTEN IoxP/IoxP MEFs are subsequently infected with a retro-viral Cre-recombinase vector (Adgene Plasmid 21654:

pMSCV PIG Cre (Puro IRES Cre vector)). This vector is produced in Phoenix cells, both Eco and Ampho ones, from Life Technology. Hereinafter the protocol is described:

Phoenix cells are transfected to 70-80% confluence with the retro-Cre vector using Lipofectamine 2000 (Invitrogen). At the same time, PTEN Ix/Ix MEFs are prepared so as to reach 70% confluence after 48 hours. 48 hours after Phoenix cells transfection their supernatant is used to infect PTEN Ix/Ix MEFs. To increase infection efficacy, Polybrene (Santa Cruz) in a 5 µg/ml concentration is used. 12 hour after the first infection, PTEN Ix/Ix MEFs are infected for the second time. 24 hours later, infected PTEN Ix/Ix MEFs are treated with 3 µg/ml puromycin as selection factor. 48 hours after incubation with puromycin, Ix/Ix MEFs that lose PTEN by Cre-recombinase and become Pten null (Pten$^{-/-}$) are selected. The afore-described features of the vector used enable a rapid and effective selection of Pten$^{-/-}$ cells.

To attain immortalization, PTEN$^{-/-}$ MEFs are infected with a TRIPZI-shp53 lentivector that is Doxocycline (DOXO) inducible. This variant enables MEF immortalization to facilitate screening procedures, costs and times. In the presence of DOXO these cells are immortal and therefore can be split indefinitely in vitro. However, when DOXO is taken away from the culture medium these cells undergo senescence due to p53 reactivation. In detail, Pten LxP/LxP MEFs, produced and cultivated as above-indicated, are first infected with a -shp53 TRIPZI Ivector that is Doxocycline (DOXO) inducible. Two days after infection, cells are selected with puromycin addition and split for various passages before being infected with pMSCV hygro-Cre (Addgene Plasmid 34565). The cells are then selected with Hygromycin for 48 h. After selection the cells become Pten$^{-/-}$; p53$^{-/-}$ in the presence of DOXO. After DOXO is taken away, MEFs become Pten$^{-/-}$; p53$^{+/+}$ and undergo senescence between day 4 and 6. The compounds and extracts to be assayed (or "HITs") are added on day 2 in order to assess their potential in increasing or arresting senescence.

The experiment ends 5 days after the administration of the candidate HITs. Positive HITs that increase proliferation of the PTEN$^{-/-}$ MEFs (proliferation is assessed by standard Crystal violet staining assay) and decrease their β-galactosidase activity (assessed by Calbiochem Senescence Detection Kit) are considered anti-senescence HITs and are selected for the next step of the assay. Positive HITs that decrease the proliferation of the PTEN$^{-/-}$ MEFs and increase their β-galactosidase activity are considered pro-senescence HITs and are also selected for the next step of the assay.

In particular, the Crystal violet staining assay is used as it is considered a simple, quick and effective test for obtaining quantitative information on the relative density of adhering cells, such as the fibroblasts used in this invention method. The dye in this assay (0.1% Crystal violet) incorporates in the DNA of cells previously fixed with 4% formaldehyde. After solubilization in 10% acetic acid, the amount of dye retaken by the monolayer is quantitated in an ELISA reader at λ=570 nm. Cellular senescence is instead visualized as the increase in cell size and pH-dependent β-galactosidase (β-Gal.) expression. To quantitate senescence present in analyzed MEFs, Calbiochem Senescence Detection Kit is used, that was designed to be able to histochemically detect β-Gal activity in culture cells at pH 6.0. This is a known feature of senescent cells. β-Gal at pH 6.0 is present only in senescent cells and is not found in pre-senescence, nor in a reversible state of growth arrest (quiescence) or in an immortal state. The mechanism of this assay is based on the greater lysosomal content of senescent cells, causing an increase of β-galactosidase enzyme.

Step 2

In the second step of the screening method, the positive compounds (HITs) selected at step 1 are added in single concentration (0.01 mg/ml) in duplicate. This step is required to assess the specificity of the compounds/extracts selected, and is very important above all for the pro-senescence compounds that will then be utilized for cancer treatment. Cancer cells have a low PTEN level, whereas primary cells have normal PTEN levels. Selected pro-senescence compounds must have no effect on primary cells, but only on cancer cells. Pten Ix/Ix MEF cells are infected with a retroviral vector containing pMSCV PIG (Puro IRES GFP vector) to obtain the puromycin-resistant Pten MEF$^{wt}$ cells, and with pMSCV PIG Cre to obtain the Pten$^{-/-}$ MEF cells, them also resistant, as described in the foregoing. Both cell types are selected with puromycin for 2 days. Compounds positive in step 1 are added to the cells, one day after selection. The experiment ends five days after the administration of the compounds to be tested. Positive compounds for which the effect on cell proliferation was confirmed in Pten$^{-/-}$ cells, but not in Pten cells, are considered "selective HITs", i.e. compounds selective for the Pten pathway, and are optionally analyzed in the next step.

Step 3

Compounds positive in step 2 are tested for their efficacy on proliferation and β-Gal activity at different dosages (five different concentrations, from lowest to highest) in Pten$^{-/-}$ MEF cells infected and selected as previously described.

Figure 1:
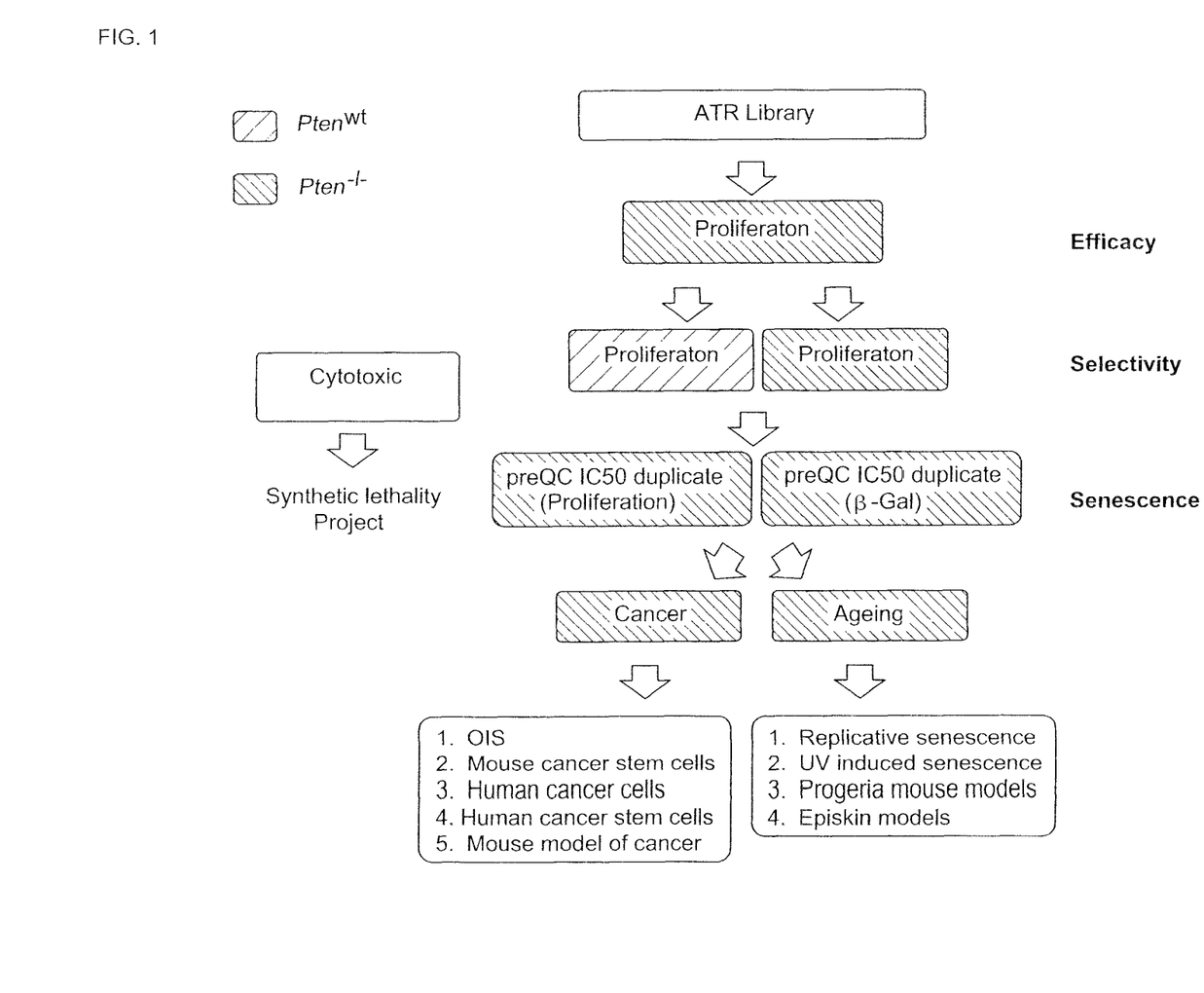
FIG. 1 is a schematic depiction of an embodiment of the method according to the present invention.

Example 2 Identification and Effectiveness of *Salvia Haenkei* Extract as Anti-Senescence Compound Among the numerous natural extracts that were tested according to the method described in Example 1 (about 500), the *Salvia Haenkei* extract (or "HAEN") showed effects on cellular proliferation in the first and second step of the method, with a statistically significant >40% increase of cell growth (FIG. 1). *Salvia Haenkei* plant material is collected and the plant parts: stalk, leaves, flowers are dried in a ventilated stove at 45° C. for 24 hours, and then ground to fine powder using an IKA universal mixer M20. An amount of 20.0 g of dried plant powder is weighted in a 100 ml conical flask to which 70 ml of hexane (degree of purity: 99%) are added for pre-extraction. The conical flask is placed in a sonicator bath (Branson 8210 or some other type) and sonicated at a temperature of 40° C. for 30 minutes. The mixture is filtered with filter paper, followed by washing with 20 ml hexane and then with 50 ml hexane. The filtrate is poured into a balloon and the solvent is concentrated under vacuum (at about 11 mm Hg) to 5-10 ml by rotavapor, using a water bath at 40° C. This residue is brought into a vessel, followed by solvent evaporation. The vessel is left open overnight under a well-ventilated hood to evaporate the last traces of solvent in the pre-extract. Solids collected on the filter are subdivided and air-dried overnight in the hood. The dried material is extracted in the same way with methanol-water (90:10). The material dried by filters set in a 100 ml conical flask to which 70 ml of 90% methanol are added. The mixture is sonicated at 40° C. for 30 minutes, after having been filtered, then washed with 20 ml of 90% ethanol. The filtrate is poured into a balloon and the solvent is completely evaporated under vacuum. The dry extract in 90% methanol is dissolved into the least possible amount of absolute methanol, using the sonicator, and poured into a 30 ml vessel to let it evaporate overnight in the hood.

Alternatively, ethanolic extraction for vegetable materials is used: *Salvia Haenkei* plant is dried in shade, and the powder produced in a mechanical grinder. The powder of vegetable material is initially degreased with petroleum benzene (60-80° C.) followed by 1000 ml of ethanol using a Soxhlet extraction apparatus for 72 hours at a temperature not higher than the boiling point of the solvent [Lin et al., 1999]. The extract is filtered using Whattman filter paper and then concentrated under vacuum and dried at 45° C. for ethanol removal. The extract is stored in sterile bottles under refrigerating conditions until the time of reconstitution.

HAEN raw extract is reconstituted in pure DMSO in the concentration of 10 um/ml, to then dilute it to the specific concentration used in the cell culture medium.

Figure 2:
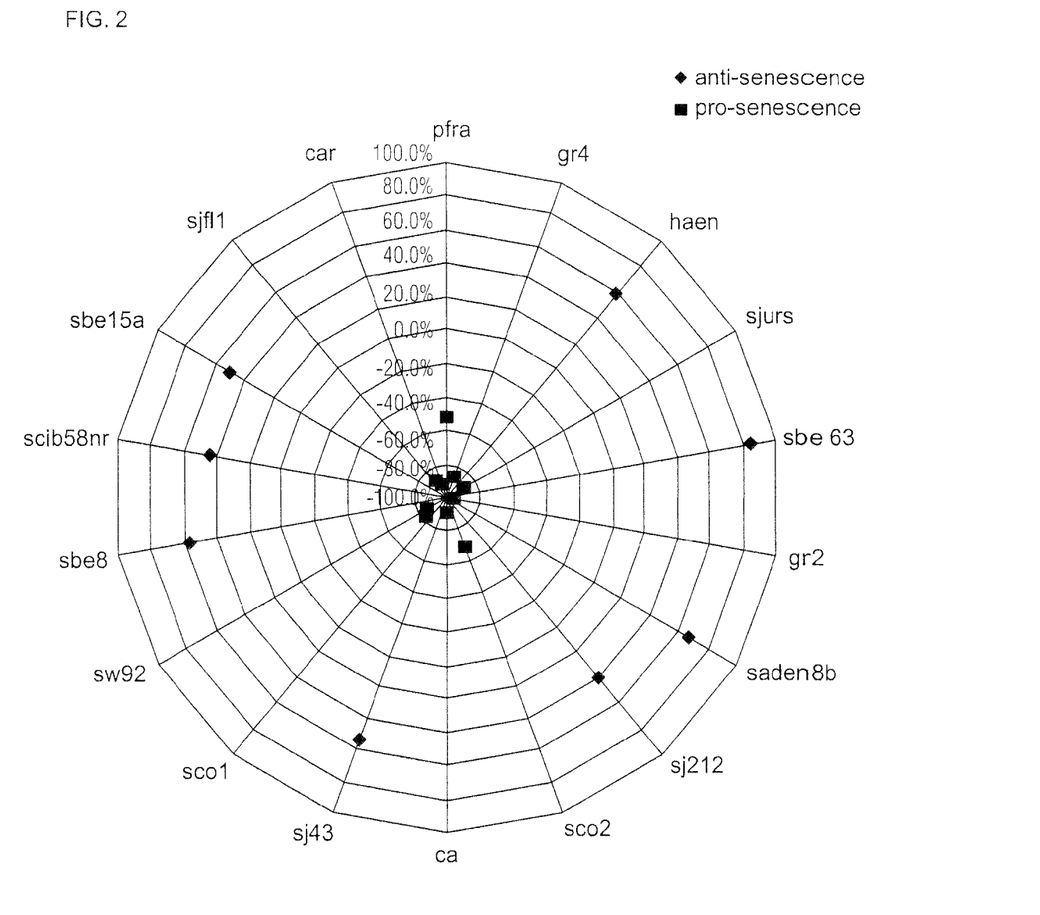

Next, the *Salvia Haenkei* extract has been tested in the 3T3 protocol in human primary cells (WI38-CCL75, ATCC) to validate the anti-senescence effect in the replicative senescence model. In detail, $3 \times 10^5$ cells were plated in 10 cm dishes and subsequently passed and re-plated in the same number every 3 days for a total of 24 passages up to the point when *Salvia Haenkei* extract (HAEN) treatment was initiated. At passage 25, cells were equally plated at $3 \times 10^5$ cells per plate and treated with the *Salvia Haenkei* extract in single concentration (0.01 mg/ml). Every 3 days cell number was determined, and then cells were re-plated at the density of $3 \times 10^5$ per plate and re-treated with *Salvia Haenkei* extract 0.01 mg/ml. At passage 30, growth arrest due to replicative senescence was observed in the untreated control group; instead, HAEN treated cells continued with replication (FIG. 2).

Figure 3:
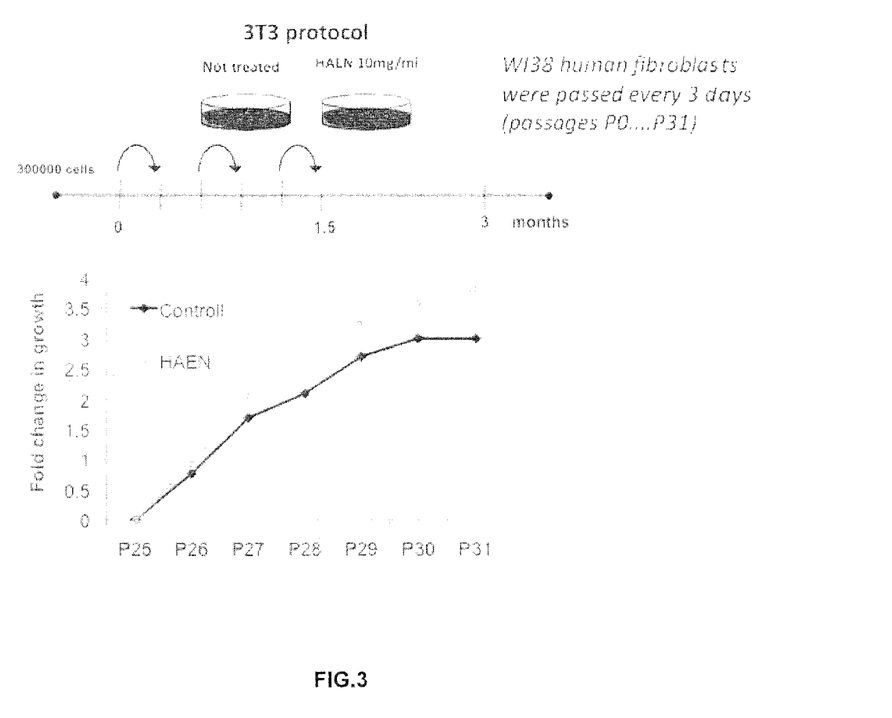
FIG. 3—Replicative senescence (3T3 protocol) in WI38 fibroblasts treated with *Salvia Haenkei* extract.

At the time points 28, 29 and 30 the cells described above were analyzed for β-galactosidase expression. The cells treated with HAEN showed a significant decrease of the number of cells positive for the senescent marker β-Gal. when compared to untreated control (FIG. 3).

Figure 4:
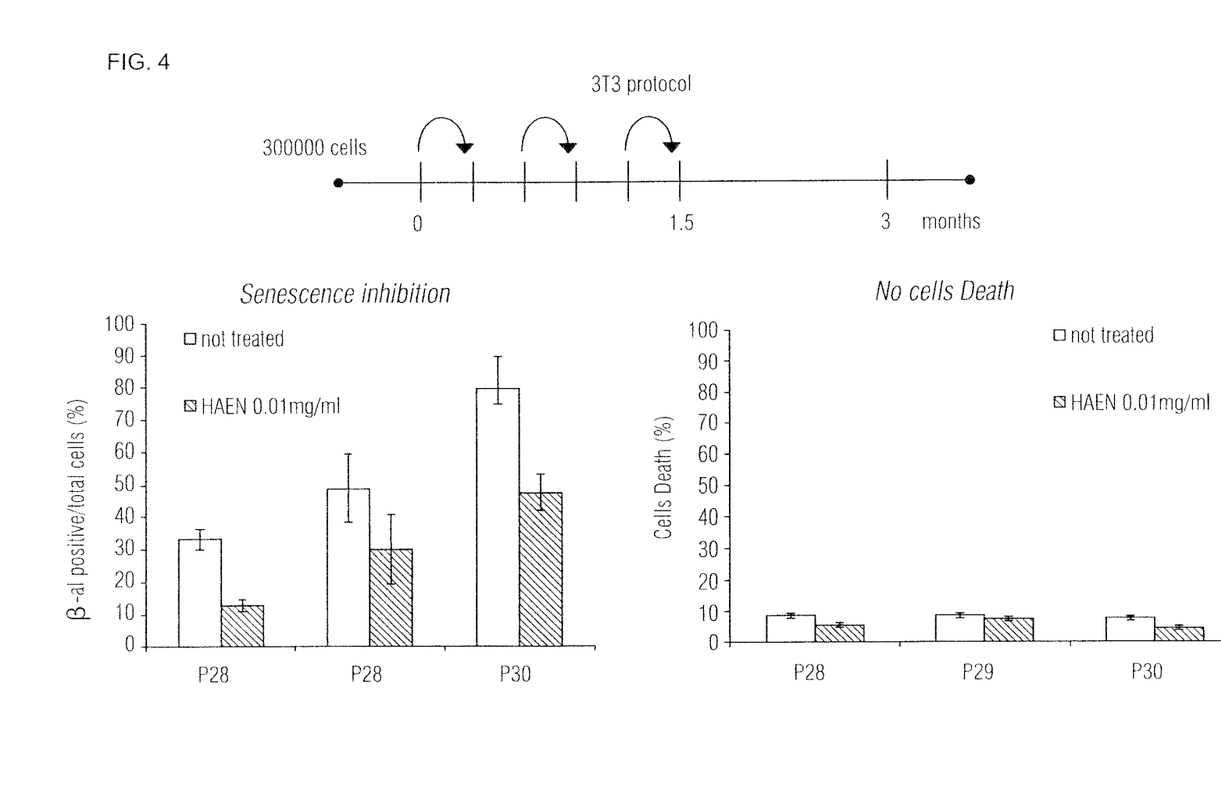
FIG. 4—Senescence and cell death in WI38 fibroblast cell cultures (Cell culture code: CCL-75tm) treated with *Salvia Haenkei* extract at different passages.
Figure 5:
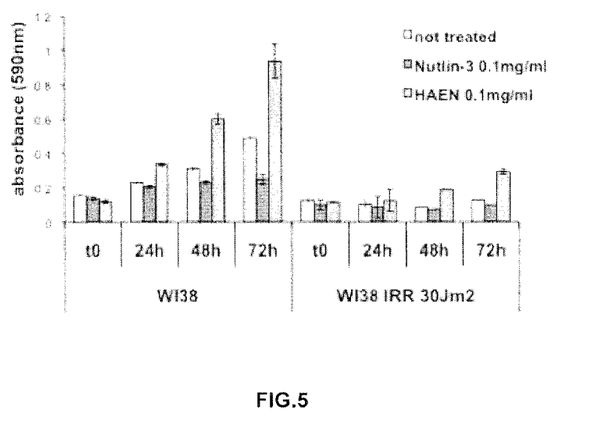
FIG. 5—Proliferation induced in primary human cell cultures (Cell culture code: CCL-75tm) treated with *Salvia Haenkei* extract and Nutlin-3 (positive control) in the UV induced senescence assay.
Figure 6:
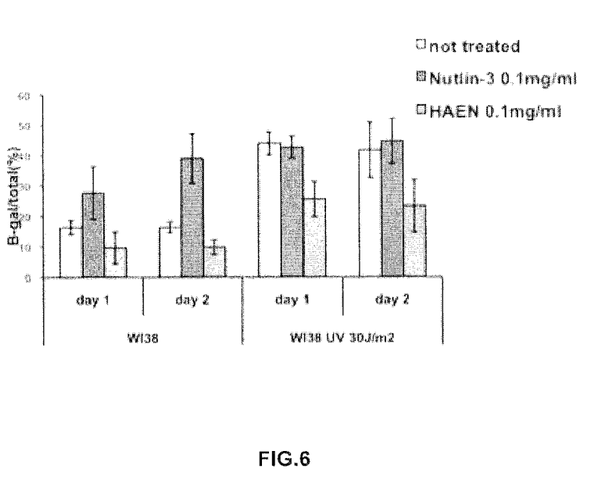
FIG. 6—Senescence in cultures of primary human cells (Cell culture code: CCL-75tm) UV treated in the presence of *Salvia Haenkei* extract.

*Salvia Haenkei* extract was also tested for the ability to prevent senescence in a model of senescence due to UVB irradiation in primary human fibroblasts (WI38-CCL75, ATCC). In summary, WI38 cells were irradiated with the optimized dose of UV irradiation that causes premature senescence. Six hours after irradiation, HAEN has been added in single concentration (0.01 mg/ml), together with the positive control treated with Nutlin-3 (0.01 mg/ml). Cell proliferation was determined at time points 24 h, 48 h and 72 h after treatment using Crystal violet assay, where intensity of colour read on spectrometer corresponds to number of live cells present in the culture. At time points 48 h and 72 h after treatment, β-Gal assay was performed to assess the presence of senescent cells in culture. HAEN treatment was able to prevent growth arrest and senescence caused by UV treatment when compared to the untreated and Nutlin-3-treated cells (FIGS. 4-5).

Figure 7:
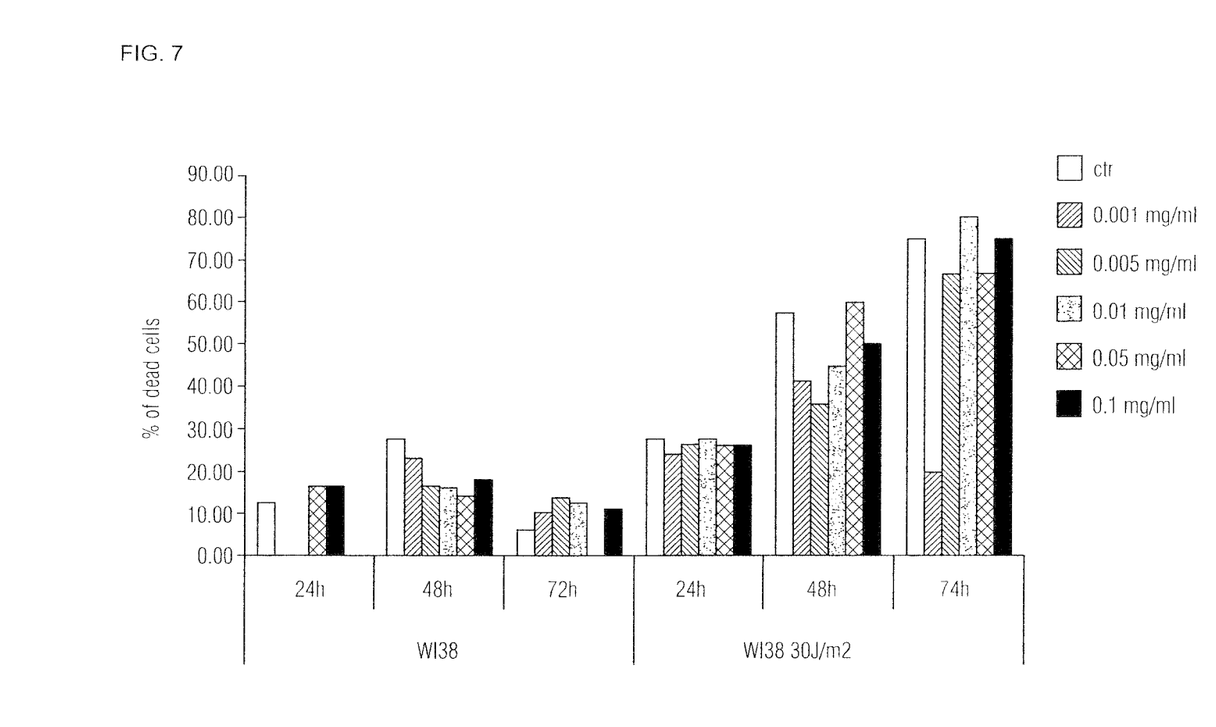
FIG. 7—Percentage of cell death in non-irradiated cells (Cell culture code: CCL-75tm) and in UV-irradiated cells in the presence of different concentrations of *Salvia Haenkei* extract.

To exclude any possibility of eventual toxic effect of HAEN and to test whether the effective dose is lower than the dose used (0.01 mg/ml) in the previous assay, WI38 cells have been treated with five different concentrations of HAEN in the presence and in the absence of UV irradiation. Cells were irradiated and analyzed for the presence of cell death by Trypan blue exclusion and proliferation levels assessed by Crystal violet staining at time points 24 h, 48 h and 72 h. HAEN showed no toxic effect when given even in concentrations 10 times higher than the effective one, 0.01 mg/ml (FIG. 7). In fact, the number of dead cells counted using Trypan blue staining was less in the HAEN treated groups when compared to the untreated control groups (FIG. 7).

Previously described experiments suggest that *Salvia Haenkei* extract (HAEN) showed to be effective as anti-senescence compound in both replicative and premature, ray-induced senescence (photo-senescence).

Figure 8:
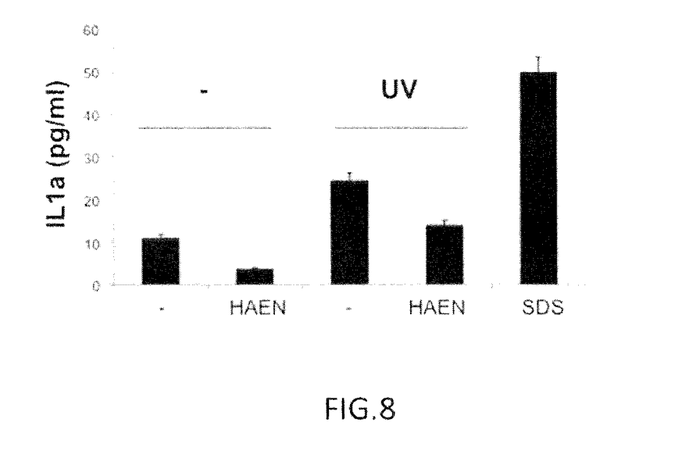
FIG. 8—IL1α in non-irradiated and UV-irradiated human skin cultivated in vitro (Episkin model) not treated or treated with *Salvia Haenkei* extract.

Finally, HAEN effect was tested on a model of human skin cultivated in vitro (Episkin model) using HAEN solubilised in oil obtained from *Olea europaea*. This extract had no toxicity on UV-irradiated human skin, and moreover did not prove to be irritating (FIG. 8). On the contrary, HAEN decreased skin levels of IL1α when compared to the control, both in non-irradiated and in irradiated skin (FIG. 8). This highlights that HAEN is able to decrease skin irritation and radiation-induced inflammation.

Figure 9:
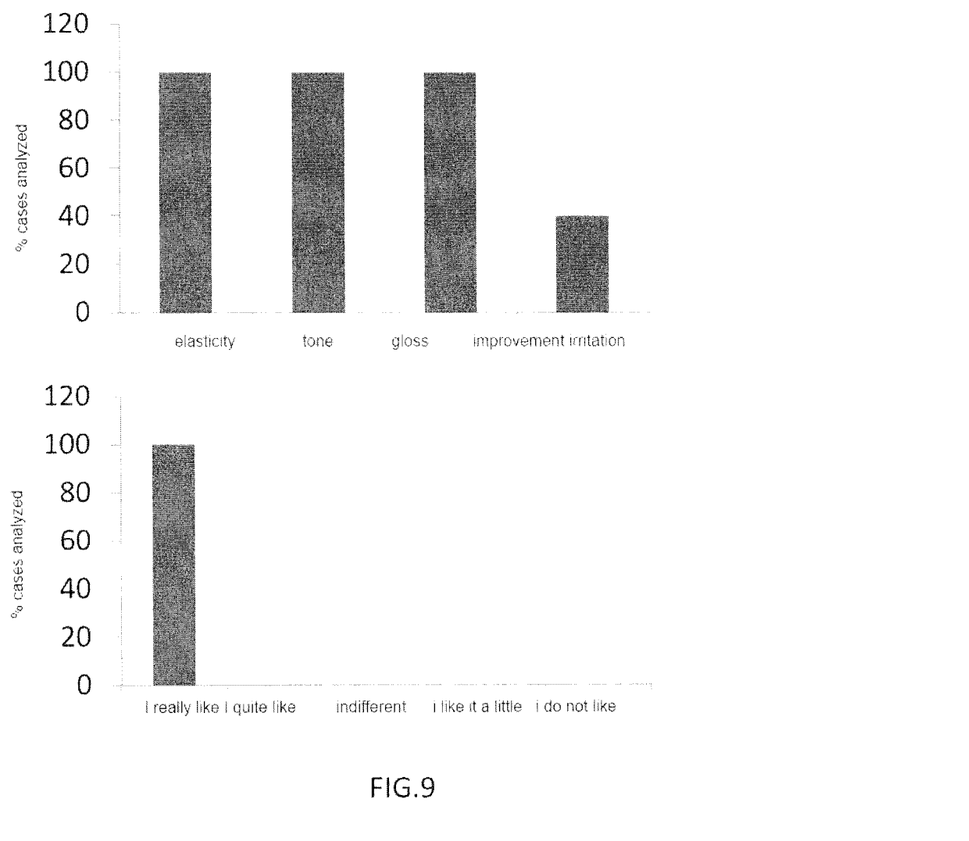
FIG. 9—Clinical trial in a group of subjects treated with *Salvia Haenkei* extract solubilised in oil.
Figure 10:
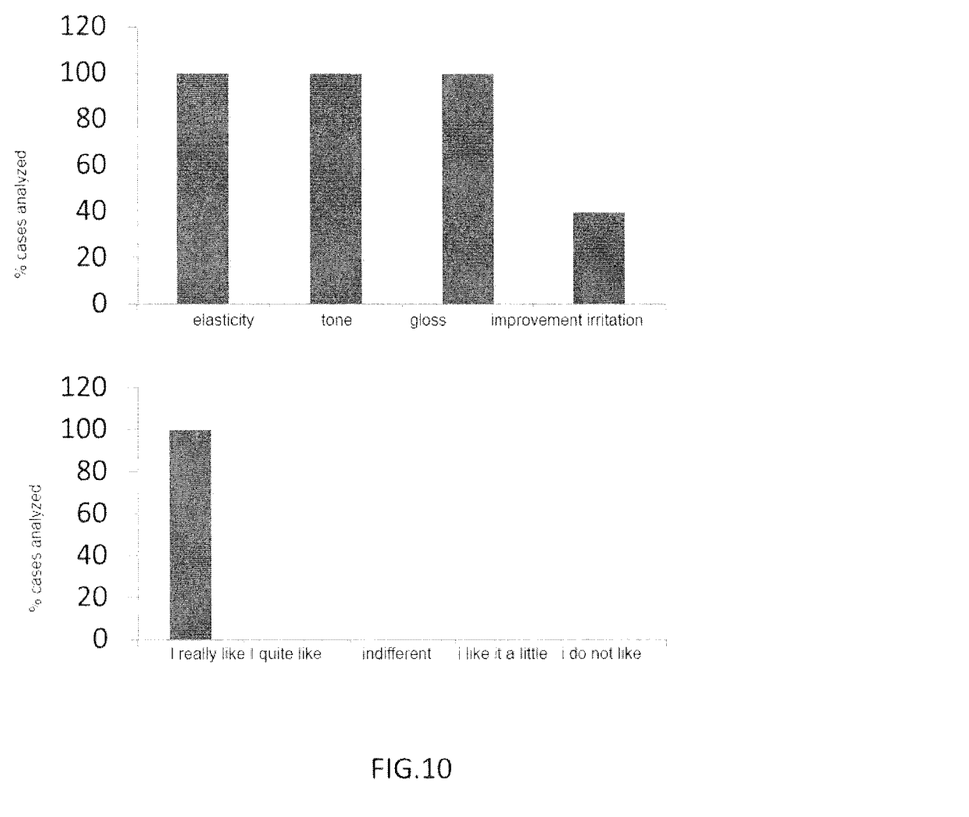
FIG. 10—Clinical trial in a group of subjects treated with *Salvia Haenkei* extract and a serum.

A clinical trial then confirmed the positive effect at the level of human skin in a group of subjects treated both with HAEN solubilised in oil obtained from *Olea europaea* and with a serum containing *Salvia Haenkei* with addition of plant Glyceria, water, gum from *caesalpinia spinosa*, *salvia officinalis* extract and *galega officinalis* extract. As demonstrated, HAEN in oil (FIG. 9) and in serum (FIG. 10) significantly improved skin luminosity, tone, elasticity of studied subjects. 40% of patients reported an improvement of skin irritation areas present prior to the treatment. Finally, most of the subjects treated observed relevant face skin improvements and considered themselves satisfied with the treatment performed (FIGS. 9-10).

Example 3 HAEN-Comprising Compositions

Specific formulation containing:
*Olea europaea* oil (96% by weight);
*Salvia officinalis* leaf essential oil (2% by weight);
*Lavandula hybrida* leaf essential oil (2% by weight);
*Salvia Haenkei* extract (prepared as described in Example 2) (0.01% by weight); the weight percentage is defined with respect to the total weight of the composition.

The invention claimed is:

1. A method of treating one or more signs of skin aging comprising administering to a subject in need thereof a cosmetic composition comprising an effective amount of *Salvia haenkei* extract.

2. The method according to claim 1, wherein said one or more signs of skin aging are selected from the group consisting of wrinkling, decrease of skin softness, and luminosity.

3. The method according to claim 1, wherein said cosmetic composition is in a form selected from the group consisting of oil, suspension, emulsion, cream, spray, ointment, powder, gel, liquid, capsule, tablet, lozenge, and serum.

4. The method according to claim 1, wherein the effective amount of the *Salvia haenkei* extract is between 0.001 and 45% by weight of said cosmetic composition.

5. The method according to claim 1, wherein the effective amount of the *Salvia haenkei* extract is between 0.01 and 4% by weight of said cosmetic composition.

6. The method according to claim 1, wherein said cosmetic composition, further comprises one or more extracts selected from the group consisting of sage, rosemary, *Galega officinalis*, lavender, *Angelica archangelica*, *Olea europaea*, and imperatonin extracts.

* * * * *